United States Patent [19]
Bayer et al.

[11] Patent Number: 5,292,814
[45] Date of Patent: Mar. 8, 1994

[54] PROCESS FOR THE PREPARATION OF MONODISPERSED POLYMER BEADS

[76] Inventors: Ernst Bayer, Bei der Ochsenweide 17; Wolfgang Rapp, Ursrainer Ring 105, both of D-7400 Tübingen, Fed. Rep. of Germany

[21] Appl. No.: 669,598

[22] Filed: Mar. 14, 1991

Related U.S. Application Data

[63] Continuation of Ser. No. 187,647, Apr. 28, 1988, abandoned.

[30] Foreign Application Priority Data

Apr. 29, 1987 [DE] Fed. Rep. of Germany ....... 3714258

[51] Int. Cl.$^5$ .......................... C08F 2/22; C08F 2/24; C08F 2/16
[52] U.S. Cl. .................... 525/243; 525/244; 525/259; 525/261; 525/266; 525/267
[58] Field of Search ................ 524/461; 525/244, 259, 525/243, 261, 266, 267

[56] References Cited

FOREIGN PATENT DOCUMENTS 0003905 9/1979 European Pat. Off. .

*Primary Examiner*—James J. Seidleck
*Assistant Examiner*—W. R. H. Clark
*Attorney, Agent, or Firm*—Bacon & Thomas

[57] ABSTRACT

The invention concerns a process for the preparation of monodispersed polymer beads, wherein in a first stage a seed polymer is prepared in an organic solvent and in the presence of an R—X compound, separated and in a second stage an emulsion polymerization is carried out in an aqueous medium in the presence of the seed polymer. The polymer beads obtained in this manner have diameters in the range of 0.5 to 50 μm, and may be used in the immobilization of proteins and cells, as carriers of catalysts and in peptide synthesis and in chromatography.

17 Claims, 3 Drawing Sheets

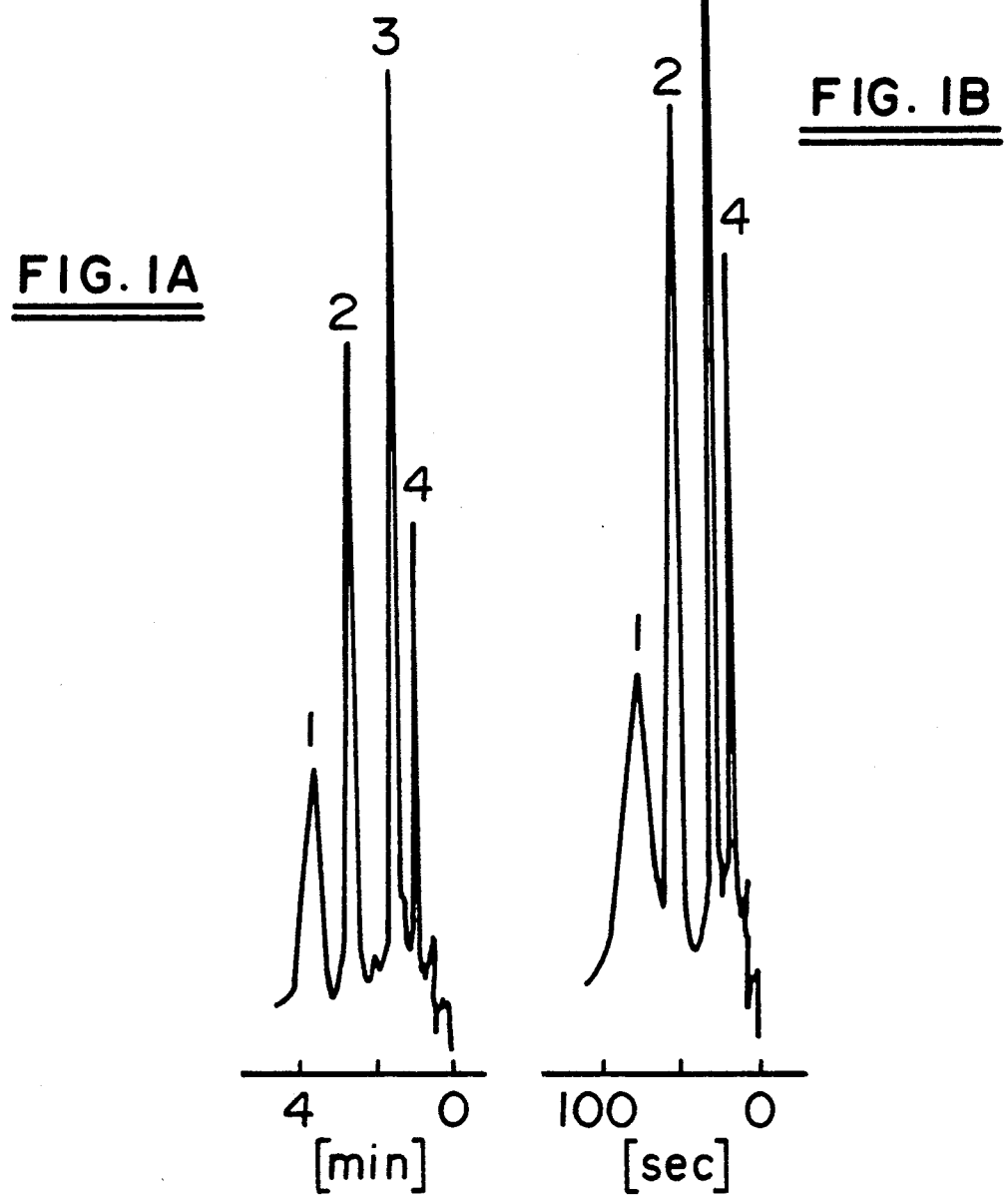

PROCESS FOR THE PREPARATION OF MONODISPERSED POLYMER BEADS

This application is a continuation of application Ser. No. 07/187,647, filed Apr. 28, 1988, now abandoned.

The invention concerns a process for the preparation of monodispersed polymer beads.

In view of their extensively inert behavior and their simple manipulation from a technical process standpoint, organic polymer carriers are finding applications at an ever-increasing rate.

In chromatographic processes, such as ion exchange chromatography, affinity chromatography and gel permeation chromatography, modified organic carriers are primarily used. The typical grain size distribution is between 5 and 40 μm.

For organic syntheses, such as nucleotide and peptide syntheses, carrier materials with diameters of 30 to 100 μm are used. Commercial ion exchangers have in part even larger diameters. For the immobilization of enzymes, carriers with large surfaces, i.e. small grain sizes, are advantageous (for example, lattices with 50-500 nm).

All of these carriers usually are polydispersed materials, i.e. materials with a broad grain size distribution. Polymer carriers with a uniform, i.e. monodispersed grain size, which generally do not vary by more than ±5%, offer clear advantages relative to polydispersed systems. As the polymer sphere represents the reaction space proper, in the case of a defined monodispersed material, uniform reaction spaces are obtained. Diffusion times and retention times are the same in each polymer bead. Similar grain sizes make possible uniform packings in chromatographic applications. In addition to the uniformity of the polymer particles, the grain size of the carrier plays an important role. The larger the radius, the lower the rate of diffusion processes in the polymer, whereby separation efficiency in chromatographic applications is reduced. Furthermore, with small diameters, the available surface is relatively larger.

Carriers with a grain size distribution of 50–1000 μm may be obtained readily with respect to process technology by emulsion polymerization. Carriers with a grain size of 50–500 μm, the so-called lattices, may be obtained by various processes. But the preparation of carriers with a grain size within a range of 0.5–50 μm, in particular 0.5 to 20 μm, which are of special interest in view of their simple manipulation in processes, is difficult.

There exist certain processes which yield monodispersed polymers with grain sizes within the range of interest. Thus, in the literature for example, a process for the preparation of polystyrene polymers in alcohols with grain sizes of 1–5 μm, is described. These monodispersed carriers contain functional groups, but are not cross-linked. Their field of application is therefore restricted to media which do not dissolve polystyrene. The mechanical stability of the polymer matrix which is not cross-linked is low.

EP-A-003 905 again describes a process for the preparation of a mono-dispersed carrier material. In this process, initially a dispersion of polymer particles in water is prepared by polymerizing a monomer in the presence of a compound that has a very low solubility in water, or by letting this low water solubility material diffuse in the polymer obtained from the monomer. It is necessary for this purpose to introduce this low water solubility substance in the reaction mixture in as fine a distribution as possible.

In a second stage, which is again carried out in an aqueous medium, partially water soluble monomers are caused to diffuse into the polymer particles, whereupon the mixture obtained in this manner is polymerized. The process described in the aforecited European application is highly complex, particularly in view of the first stage, and frequently is not reproducible.

It is therefore the object of the present invention to provide a process for the preparation of monodispersed polymer beads making possible the production of polymer beads with diameters within a range of 0.5 to 50 μm, in a simple and reliable manner.

The process also makes it further possible to prepare polymer beads with variable properties. For example, it should be possible to produce polymer beads with an arbitrary porosity, cross-linked or not cross-linked, and with or without functional groups.

It has now been discovered that this object may be attained by preparing a seed polymer in an organic solvent in the presence of certain organic compounds.

The invention thus concerns a process for the preparation of monodispersed polymer beads with a diameter in a range of 0.5 to 50 μm, characterized in that:

In a first stage a polymer seed is prepared, by polymerizing a monomer yielding a monodispersed seed polymer in an organic solvent or a mixture of solvents, in the presence of triphenylmethane or a compound of the formula R—X, wherein R signifies a saturated or unsaturated, linear or branched alkyl radical with more than 6 carbon atoms and X stands for a hydrogen or halogen atom or a hydroxy group, a $C_1$–$C_6$ alkoxy group, an amino group, a $C_1$–$C_6$ alkylamino group, a di-$C_1$–$C_6$ alkylamino group, a phenyl group or a phenyl group substituted by a $C_1$–$C_4$ alkyl group, a hydroxy group optionally polyoxyethylenated, or a sulfonic acid group, in the presence of a polymerization initiator, and separating the seed polymer obtained; and In a second stage an emulsion polymerization is carried out by polymerizing a monomer in the presence of the seed polymer, an emulsifier, a polymerization initiator and optionally a cross-linking agent in an aqueous medium.

According to the invention, the seed polymer is prepared in the first stage in an organic solvent producing a monodispersed seed. This solvent preferably is an alcohol, particularly a linear or branched $C_1$–$C_6$ alcohol, and preferably a $C_1$–$C_4$ alcohol, such as methanol, ethanol or t-butanol. The organic solvent may consist of an individual solvent or a mixture of several solvents.

The organic solvent may also be used in a mixture with another solvent that does not lead to the formation of a monodispersed seed. This other solvent serves to modify the solution behavior. By the addition of such different solvents, the particle size of the seed polymer formed may be controlled. By using such a different solvent, seed polymers with a larger particle diameter are obtained. The proportion of the other solvent generally amounts to 20% by volume, preferably 5 to 15% by volume.

Suitable solvents that may be added to a solvent to produce a monodispersed seed polymer, in particular, are hydrocarbons, such as pentane and hexane; aromatic hydrocarbons, such as toluene, o-, m- and p-xylene; chlorinated hydrocarbons, such as methylene chloride and chloroform; ketones, such as acetone and methylethylketone; esters, such as ethyl acetate; and ethers, such as tetrahydrofuran and dioxan. Water may also be added, particularly if alcohols are used, provided the mixture remains homogeneous. Generally, a maximum of 10% by volume of water may be added as a function of the type of the organic solvent, the R—X compound, and of the monomer.

As a further component for the preparation of the seed polymer, a compound of the formula R—X is added. Here, R stands for a saturated or unsaturated, linear or branched alkyl radical with more than 6 carbon atoms and X signifies a hydrogen or halogen atom (in particular a chlorine or bromine atom), a hydroxy or $C_1$–$C_6$ alkoxy group, an amino $C_1$–$C_6$ alkylamino group or a di-$C_1$–$C_6$ alkylamino group, a phenyl group or a phenyl group substituted by a $C_1$–$C_4$ alkyl group, a hydroxy group optionally polyoxyethylenated, a $C_1$–$C_4$ alkoxy group, an amino group or a sulfonic acid group.

Preferably, a compound of the formula R—X, wherein R is a saturated, preferably linear alkyl radical with 7 to 20 carbon atoms, in particular 9 to 18 carbon atoms, is used. Examples of such R radicals are the linear $C_9$-, $C_{10}$-, $C_{12}$-, $C_{14}$-, $C_{16}$- and $C_{18}$- alkyl radicals. But mixtures of such radicals may also be present.

Preferably, in the R—X formula, X stands for a halogen atom (in particular a chlorine atom) or a hydroxy, amino, phenyl or substituted phenyl group. In a particularly preferred manner, X signifies a halogen atom or a phenyl group.

Examples of particularly preferred R—X compounds are nonylbenzene or dodecylchloride. The use of triphenylmethane is also preferred, because the seed polymer may be handled in an especially simple manner if this compound is employed.

The use of compounds of the R—X formula, wherein R is an unsaturated radical, is advantageous when it is desired to prepare cross-linked monodispersed polymer beads.

The monomers used in the first stage of the preparation of the seed polymer very generally may consist of vinyl monomers. However, two or more polymers may also be used, so that a copolymer is obtained. Preferably, styrene or functionalized styrene, for example, styrene functionalized with chormethyl, sulfonic acid or amino groups, is employed. Additional suitable monomers are acrylic acid derivatives, such as acrylic acid, acrylamide, acrylonitrile and the corresponding methacrylic acid derivatives, and the like. The seed polymer is prepared in the presence of a polymerization initiator, which is one of the compounds customarily used in this field. Suitable examples are azoisobutyronitrile (AIBN) and peroxides, such as benzoylhydroperoxide and benzoylperoxide.

The usual auxiliary substances may further be used in the preparation of the seed polymer, for example, protective colloids, such as polyvinylpyrrolidone (molecular weight approximately 1,000,000) and polyvinylalcohol.

The proportion of the monomer and the R—X compound depends upon the type of these components and on the solvent used. Generally, however, the ratio of the monomer to the R—X compound is within a range of 1:0.1 to 1:3.

The quantity of the solvent is generally chosen so that about 10 to 20% by weight of the monomer is contained in the solvent.

The temperature for the preparation of the seed polymer is chosen generally as a function of the solvent. It is generally between 50° to 100° C., preferably 60° to 90° C. The reaction time may amount to up to 48 h and is preferably between 24 to 48 h.

A monodispersed seed polymer with a particle size between 0.5 to 10 $\mu$m, preferably 1 to 5 $\mu$m, is obtained in this manner. It is also possible to control the particle size by the quantity of the R—X formula. The higher the proportion of this compound, the larger the particle size of the seed polymer.

The seed polymer obtained in this manner is separated and isolated in a conventional manner, for example, by centrifuging.

In the second stage of the process according to the invention, emulsion polymerization is carried out, using the seed polymer obtained. Polymerization takes place in an aqueous medium with the addition of an emulsifier and a polymerization initiator. The usual emulsifiers employed in this field are used, for example, an alkylsulfonic acid, such as hexadecanesulfonic acid or the product with the commercial designation of K-30 ($C_{12}$–$C_{14}$ sulfonic acid) of BASF.

The polymerization initiator, which must be soluble in oil, again may be one of the compounds customarily employed in this field, for example, a compound cited relative to the first stage.

The monomer to be used here generally is a polymerizable vinyl compound, which may be difunctional (for cross-linking). Preferably, these are monomers described in connection with the first stage. The monomers used in the first and the second stage may be identical or different.

For the preparation of cross-linked polymer beads, in the second stage a cross-linking agent is also used. For the purpose, conventional cross-linking agents, such as divinylbenzene, bifunctional acrylic compounds, and the like, may be employed, but cross-linking may also be effected by applying functionalized monomers. A preferred functionalized monomer is chloromethylated styrene. Cross-linking is effected by the addition of a Friedel-Crafts catalyst, such as aluminum chloride.

In order to vary the structure of the monodispersed polymer beads, in the second stage, an inert compound that does not polymerize, may be added. This inert component must be such that it diffuses into the seed polymer and may be removed after the completion of the polymerization by suitable measures, such as washing, evaporation by heating or in a vacuum, and the like.

If, as the inert component a solvent of the polymer (seed polymer) is used, microporous polymer beads are obtained. If, on the other hand, an inert component is used that is not a solvent of the polymer, macroporous polymer beads are obtained.

Suitable inert components are higher aliphatic, cyclic or aromatic hydrocarbons, such as heptane, octane, cyclohexane, benzene, toluene, o-, m-, p-xylene, ethylbenzene and the like; higher alcohols, such as hexanol, heptanol, octanol, decanol and the like; cyclic alcohols, such as cyclohexanol and the like, chlorinated hydrocarbons, such as dichloromethane and chloroform and the like. The inert component may be added individually or in a mixture. The selection of a suitable solvent is a function of the polymer. By choosing an appropriate solvent or a suitable mixture of solvents, it is therefore possible to vary the solvent properties of the inert component and, as such, the porosity of the polymer beads as desired. In this manner, polymer beads with a pore size of about 5 Å to approximately 3000 Å may be produced.

For the emulsion polymerization of the second stage, the seed polymer is used in quantities of 1 to 20% by weight, preferably, 1-15 % by weight, relative to the quantity of the monomer.

Cross-linking agents are used in a proportion relative to the quantity of the monomer of 0.1 to 60% by weight, depending on the degree of cross-linking desired. Advantageously, 60% divinylbenzene in ethylvinylbenzene is used.

The components introduced into the aqueous medium diffuse into the seed polymer. The seed polymer particles are thus present in a swollen state in the monomer. Polymerization then takes place in the seed polymer particles.

Polymerization is carried out at a temperature up to a maximum of 100° C., preferably at 60° to 90° C. The time of the polymerization generally varies up to 48 h and is preferably between 24 and 48 h.

The process according to the invention thus yields in a simple manner monodispersed polymer beads with a particle diameter of 0.5 to 50 μm, preferably 1 to 20 μm and particularly preferably from 1 to 10 μm. The polymer particles may be cross-linked or not cross-linked. Their porosity may be varied by the conditions of the process.

The polymer beads that may be obtained by the process of the invention therefore have a wide field of application. They may be used in particular for the immobilization of proteins (enzymes) and cells (for whole cells), as carriers of catalysts (biocatalysts, organic or inorganic catalysts) or as carriers in peptide synthesis. For peptide synthesis in particular, polymer beads forming a gel are used, i.e., lightly cross-linked polymer beads with a degree of cross-linking of 1 to 5%, preferably 1 to 2%.

The monodispersed polymer beads according to the invention are especially suitable for use in chromatography. They are employed specifically in high pressure liquid chromatography (HPLC), ion exchange chromatography and exclusion chromatography.

BRIEF DESCRIPTION OF THE DRAWINGS

In the drawings:

FIG. 1A and FIG. 1B show a HPLC chromatogram obtained with polymer beads according to the invention as the stationary phase.

Figure 2A:
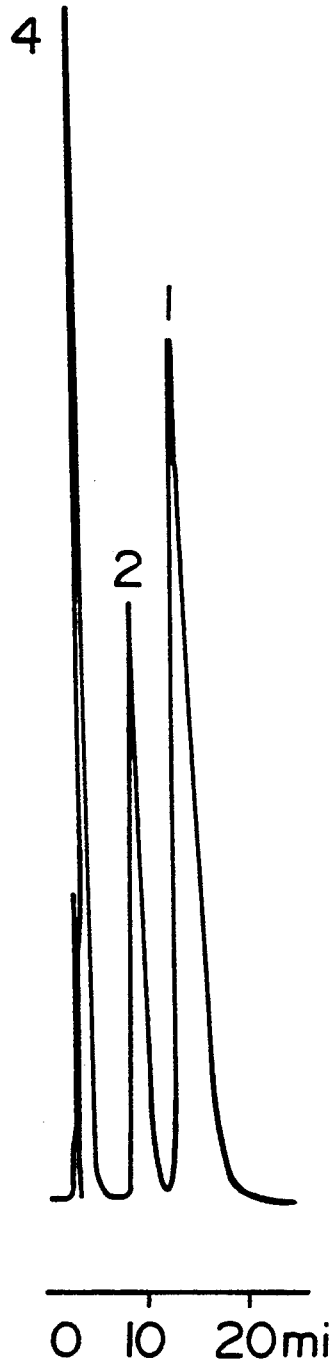
FIG. 2A and FIG. 2B show an HPLC chromatogram obtained with commercially available polymer beads as the stationary phase.

The following examples are intended to explain the invention without limiting it.

EXAMPLE 1

In 480 ml ethanol, 384 azoisobutyronitrile (AIBN) and 2.4 g polyvinylpyrrolidinone (PVP) are dissolved. To the solution, 30 ml styrene and 30 ml dodecylchloride are added. The polymerization temperature is 60° C. After a reaction time of 24 h, a monodispersed polystyrene latex with a grain size of 1.8 μm, containing about 12% dodecylchloride, is obtained.

Solids content: 1 ml polystyrene/10 ml solution - 635 mg latex.

EXAMPLE 2

In 24 ml ethanol, 12.2 mg AIBN and 120 mg PVP are dissolved. 1.5 ml styrene and 2.4 ml dodecylchloride are added and heated to 60° C. After 16 h, another solution of 2 ml styrene and 50 mg AIBN in 2 ml ethanol is added. After another 5 h of reaction time, 50 mg PVP in 5 ml ethanol are added and polymerized for another 24 h. A monodispersed polystyrene with a grain size of 2.5 μm is obtained. The seed polymer contains 12% dodecylchloride.

EXAMPLE 3

10 ml of the seed solution prepared in Example 2 are centrifuged for 20 min at 2000 rpm and the organic phase decanted. To the residue an aqueous emulsion of 250 mg alkylsulfonic acid, 0.4 ml divinylbenzene, 3 ml chloromethylstyrene, 17 ml styrene and 250 mg BPO (benzoylperoxide) in 180 ml water, are added. The mixture is agitated at 120 rpm for 24 h at room temperature and subsequently for another 48 h at 72° C. The monodispersed copolymers obtained in this manner have a diameter of 7.8 μm and a chlorine content of 4% = 1.14 meq Cl/g.

EXAMPLE 4

250 mg emulsifier (alkylsulfonic acid) are dissolved in 165 ml water and 3.3 ml chloromethylstyrene, 4 ml divinylbenzene, 14.5 ml styrene and 250 mg BPO are emulsified therein. From 30 ml of a solution of the latex prepared in Example 1, the solids are separated as in Example 3, and mixed with the aqueous emulsion of the monomers.

The mixture is agitated for 18 h at room temperature at 100 rpm and then the temperature is raised to 72° C. After 48 h, a monodispersed product with a chlorine content of 4.47% = 1.27 meq Cl/g is obtained. The grain size is 4.2 μm.

EXAMPLE 5

In 48 ml ethanol, 38.4 g AIBN and 240 mg PVP are dissolved. 3 ml styrene and 3 ml nonylbenzene are added, flushed with argon and heated in 24 h to 72° C. The monodispersed polystyrene latex has a grain size of 2 μm.

EXAMPLE 6

From 10 ml of the seed solution prepared in Example 5, the polymer component is obtained by centrifuging. An emulsion is prepared, which contains 16 ml water, 110 mg alkylsulfonic acid, 8.5 ml styrene, 2.6 ml divinylbenzene/ethylvinylbenzene, 2.2 ml chloromethylstyrene and 160 mg BPO. The seed polymer is mixed with the monomer emulsion, agitated for 24 h at room temperature and heated under an inert gas to 75° C. After a reaction time of 48 h a monodispersed carrier with a grain size of 5.9 μm is obtained. The chlorine content is 1.25 meq/g.

EXAMPLE 7

A monomer emulsion is prepared, containing 83 mg BPO, 1.1 ml chloromethylstyrene, 1.3 ml divinylbenzene/ethylvinylbenzene, 4.2 ml styrene, 8.3 ml water and 83 mg alkylsulfonic acid. Further processing is similar to Example 6. A monodispersed carrier with a grain size of 4.5 μm is obtained. Chlorine content: 1.26 meq/g.

EXAMPLE 8

In 100 ml methanol, 500 mg PVP and 80 mg AIBN are dissolved. To the solution, 6.25 ml styrene and 6.25 ml dodecylbenzene are added, flushed with argon and heated under agitation at 48 h to 62° C. A monodispersed latex with a grain size of 2.5 μm is obtained. The latex contains 46% dodecylbenzene.

The latex is isolated by centrifuging and mixed with a monomer emulsion of 940 mg emulsifier K-30, 62.5 ml water, 10.8 ml divinylbenzene/ethylvinylbenzene (60/40), 48.2 ml styrene and 800 mg benzoylperoxide. The emulsion is homogenized in an ultrasonic bath. Diffusion is effected for 2 h at room temperature, the temperature raised to 80° C. and this temperature maintained for 48 h. Polystyrene beads with a grain size of 8.5 μm are obtained in this manner.

EXAMPLE 9

In 100 ml ethanol, 500 mg PVP and 80 mg AIBN are dissolved. The solution is mixed with 7.2 ml styrene and 6.25 ml stearylalcohol, flushed with argon and polymerized for 48 h at 75° C. The latex has a grain size of 1 μm.

The latex is then treated as in Example 8 and polystyrene beads with a grain size of 2.5 μm are obtained.

EXAMPLE 10

In 100 ml t-butanol, 500 mg PVP and 80 mg AIBN are dissolved. The solution is mixed with 6.25 ml styrene and 3.3 g triphenylmethane, flushed with argon and heated under agitation to 77° C. The monodispersed latex has a diameter of 1.5 μm.

The latex is treated as in Example 9 and polystyrene beads with a grain size of 4.8 μm are obtained.

EXAMPLE 11

To a solution of 100 ml t-butanol, 500 mg PVP and 80 mg AIBN, 12.5 ml dodecylbenzene and 6.25 ml styrene are added. After flushing with argon, the mixture is heated to 75° C. and the temperature maintained for 48 h. The seed has a grain size of 4 μm and a dodecylbenzene content of 50%.

The latex is then treated as in Example 9 and polystyrene beads with a grain size of 9.2 μm are obtained.

EXAMPLE 12

To a solution of 25 ml ethanol, 20 mg AIBN, 125 mg polyvinyl alcohol (PVA), 5 ml THF and 1.56 ml styrene are added. The mixture is heated to 70° C. for 40 h and a 5 μm latex is obtained.

EXAMPLE 13

To a solution consisting of 60 ml ethanol, 6.4 ml water, 300 mg PVP and 48 mg AIBN, 7.5 ml styrene and the same quantity of dodecylchloride are added. The mixture is heated to 74° C. for 48 h. A latex of 750 nm is produced in this manner.

The latex is treated as in Example 9 and polystyrene beads with a grain size of 2.2 μm are obtained.

EXAMPLE 14

600 ml ethanol are mixed with 3 g PVP and 480 mg AIBN. To the clear solution, 75 ml dodecylchloride and 75 ml styrene are added. The mixture is heated to 72° C. for 48 h.

The grain size of the monodispersed latex is 2.2 μm.

EXAMPLE 15

From 120 ml of the latex suspension described in Example 14, the polystyrene latex is separated by centrifuge (9.9 g latex).

The seed latex is mixed with a finely divided emulsion consisting of 160 ml water, 2.2 g alkylsulfonic acid (K-30), 16 ml divinylbenzene/ethylvinylbenzene (60/40), 64 ml styrene, 80 ml heptane and 1 g BPO. The emulsion is produced by ultrasonic treatment.

Diffusion is effected for 30 min at room temperature under agitation, the suspension is diluted with 600 ml water, flushed with argon and heated to 80° C. for 45 h.

A microporous, cross-linked polymer with a grain size of 5.5 μm is obtained.

EXAMPLE 16

A seed latex is prepared as in Example 15. The seed latex is mixed with a finely divided emulsion, consisting of 160 ml water, 2 g alkylsulfonic acid (K-30), 128 ml divinylbenzene/ethylvinylbenzene (60/40), 32 ml styrene and 2.0 g benzoylperoxide. The emulsion is produced by ultrasonic treatment. Diffusion is effected in 45 min at room temperature, the suspension diluted with 600 ml water, flushed with argon and heated to 80° C. for 45 h. A homogeneously cross-linked polymer with a grain size of 4.5 μm is obtained.

EXAMPLE 17

In the following experiments, polymer beads obtained according to the invention (MOPS 33/4; polystyrene/40% divinylbenzene; prepared according to Example 16) are used as the stationary phase in HPLC chromatography. As a comparison, two commercial products are also used as the stationary phase, i.e. ACT-1 (commercial product of the Interaction Co.; polystyrene modified with $C_{18}$-alkyl) and PRP (commercial polystyrene-reverse phase). The phases were used under the following conditions:

MOPS 33/4

Mobile phase: acetonitrile/water 85/15
Grain size: 4.5 μm
Column: 60×4.5
Flow: 1 ml/min and 2 ml/min, respectively
Pressure: 32 bar

ACP-1 and PRP

Mobile phase: 85% methanol
Flow: 6 cm/min
Column: 125×4.6

Figure 2B:
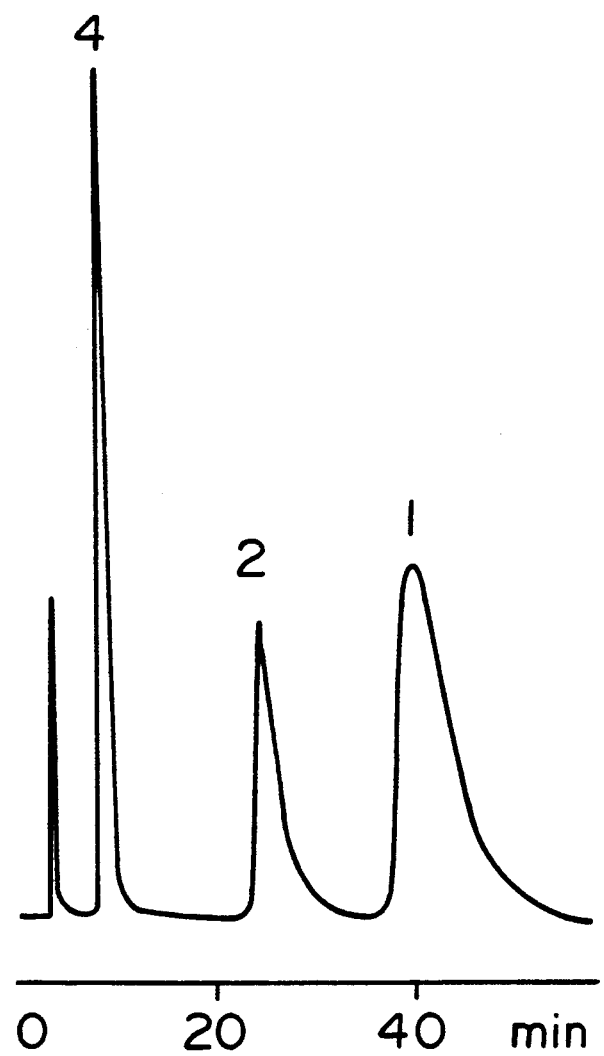

Detection was effected in all cases at 254 nm.
The following product mixture was separated.
1. N,N-diethylaniline
2. N,N-dimethylaniline
3. N-methylaniline
4. aniline The chromatograms obtained are compiled in FIG. 1 and FIG. 2. It is seen that the phases according to the invention (FIG. 1) have a significantly higher separation efficiency, as in spite of an appreciably shorter column they yield good separation. In addition, the use of the phases according to the invention clearly improves the peak symmetry, while the phases of the state of the art show pronounced tailing.

Figure 3:
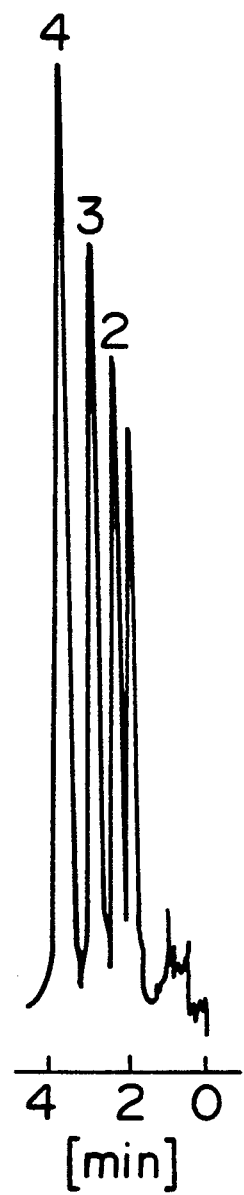
FIG. 3 shows another HPLC chromatogram obtained with polymer beads according to the invention as the stationary phase.

FIG. 3 shows a chromatogram obtained with the use of the same phase according to the invention in the separation of the following product mixture:

1. toluene
1. ethylbenzene
3. propylbenzene
4. butylbenzene

We claim:

1. A process for the preparation of monodispersed polymer beads having a diameter of 0.5 to 50 μm, wherein, in a first homogeneous stage, a seed polymer is prepared by polymerizing a monomer dissolved in at least one organic solvent, yielding a monodispersed seed, in the presence of a polymerization initiator and triphenylmethane or a compound having the formula R—X, wherein R is a saturated or unsaturated, linear or branched aliphatic radical with more than 6 carbon atoms, and X is selected from the group consisting of a hydrogen, halogen atom, a hydroxy group, a $C_1$-$C_6$ alkoxy group, an amino group, a $C_1$-$C_6$ alkylamino group, a di-$C_1$-$C_6$ alkylamino group, a phenyl group or a phenyl group optionally substituted with a $C_1$-$C_4$ alkyl group, a polyoxyethylenated hydroxy group or a sulfonic acid group;

separating the seed polymer obtained; and wherein, in a second stage, an emulsion polymerization is carried out by polymerizing a monomer in the presence of the seed polymer, an emulsifier, a polymerization initiator and optionally a cross-linking agent, in an aqueous medium.

2. A process according to claim 1, wherein an alcohol is used as the organic solvent.

3. A process according to claim 1, wherein, in the second stage an inert, nonpolymerizing compound is added.

4. Monodispersed polymer beads obtained by a process according to claim 1.

5. A process for the preparation of monodispersed polymer beads having a diameter of 0.5 to 50 μm, wherein, in a first homogenous stage, a seed polymer is prepared by polymerizing a monomer dissolved in at least one alcohol, which is a solvent for the monomer, yielding a monodispersed seed, in the presence of a polymerization initiator and a compound having the formula R—X, wherein R is a $C_7$-$C_{20}$ alkyl radical and X is selected from the group consisting of a halogen atom, a phenyl group or a phenyl group optionally substituted with a $C_1$-$C_4$ alkyl group;

separating the seed polymer obtained; and wherein, in a second stage, an emulsion polymerization is carried out by polymerizing a monomer in the presence of the seed polymer, an emulsifier, a polymerization initiator and a cross-linking agent, in an aqueous medium and wherein, in said second stage, an inert, nonpolymerizing compound is added and subsequently removed after polymerization.

6. A process according to claim 5 wherein the alcohol is $C_1$-$C_4$ alcohol.

7. A process according to claim 6 wherein the alcohol is selected from the group consisting of methanol, ethanol or t-butanol.

8. A process according to claim 5 wherein R is a $C_9C_{18}$ alkyl radical.

9. A process according to claim 5 wherein X is selected from the group consisting of a halogen atom or a phenyl group.

10. A process according to claim 5 wherein the R—X compound is selected from the group consisting of nonylbenzene or dodecylchloride.

11. A process according to claim 5 wherein the cross-linking agent is selected from the group consisting of divinylbenzene, bifunctional acrylic compounds, functionalized styrenes or mixtures thereof.

12. Monodispersed polymer beads obtained by a process according to claim 5.

13. A process for the preparation of monodispersed polymer beads having a diameter of 0.5 to 50 μm, wherein, in a first homogenous stage, a seed polymer is prepared by polymerizing a monomer dissolved in at least one alcohol, which is a solvent for the monomer, yielding a monodispersed seed, in the presence of a polymerization initiator and a compound having the formula R—X, wherein R is a $C_7$-$C_{20}$ alkyl radical and X is selected from the group consisting of a halogen atom, a phenyl group or a phenyl group optionally substituted with a $C_1$-$C_4$ alkyl group;

separating the seed polymer obtained; and wherein, in a second stage, an emulsion polymerization is carried out by polymerizing a monomer in the presence of the seed polymer, an emulsifier, a polymerization initiator and a bifunctional monomer cross-linking agent, in an aqueous medium and wherein, in said second stage, an inert, nonpolymerizing compound is added and subsequently removed after polymerization.

14. A process according to claim 13 wherein the bifunctional monomer cross-linking agent is divinylbenzene.

15. The process of claim 1 wherein the seed polymer formed in said first homogeneous stage has a diameter of 1.0 to 5 μm.

16. The process of claim 5 wherein the seed polymer formed in said first homogeneous stage has a diameter of 1.0 to 5 μm.

17. The process of claim 13 wherein the seed polymer formed in said first homogeneous stage has a diameter of 1.0 to 5 μm.

* * * * *